(12) United States Patent
Cai et al.

(10) Patent No.: US 10,106,595 B2
(45) Date of Patent: Oct. 23, 2018

(54) NUCLEIC ACID SEQUENCE ENCODING A FUSION PROTEIN

(71) Applicant: VIVA BIOTECH (SHANGHAI) LTD., Shanghai (CN)

(72) Inventors: Jianhua Cai, Shanghai (CN); Jian Shen, Shanghai (CN); Fan Jiang, Shanghai (CN); Na Li, Shanghai (CN); Wentao Wei, Shanghai (CN); Xiuhong Zeng, Shanghai (CN); Xiaoyan Su, Shanghai (CN); Min Han, Shanghai (CN); Delin Ren, Shanghai (CN); Chen Mao, Shanghai (CN)

(73) Assignee: VIVA BIOTECH (SHANGHAI) LTD., Shanghai (CN)

( * ) Notice: Subject to any disclaimer, the term of this patent is extended or adjusted under 35 U.S.C. 154(b) by 66 days.

(21) Appl. No.: 15/494,551

(22) Filed: Apr. 24, 2017

(65) Prior Publication Data

US 2017/0226187 A1    Aug. 10, 2017

Related U.S. Application Data

(60) Division of application No. 14/633,153, filed on Feb. 27, 2015, which is a continuation-in-part of application No. PCT/CN2014/070537, filed on Jan. 13, 2014.

(30) Foreign Application Priority Data

Nov. 18, 2013    (CN) .......................... 2013 1 0577289

(51) Int. Cl.
*C12N 15/12* (2006.01)
*C12N 15/62* (2006.01)
*C12N 15/63* (2006.01)
*C07K 14/72* (2006.01)
*C07K 14/47* (2006.01)
*C07K 14/435* (2006.01)

(52) U.S. Cl.
CPC ...... *C07K 14/723* (2013.01); *C07K 14/43545* (2013.01); *C07K 14/4703* (2013.01); *C07K 14/4738* (2013.01); *C07K 2319/35* (2013.01)

(58) Field of Classification Search
None
See application file for complete search history.

(56) References Cited

U.S. PATENT DOCUMENTS

2011/0207146 A1*  8/2011  Perez ................. G01N 33/5008
                                                            435/7.2

* cited by examiner

*Primary Examiner* — Michael Pak
(74) *Attorney, Agent, or Firm* — JCIPRNET

(57) ABSTRACT

The present invention relates to fusion proteins for the expression of G-protein coupled receptor proteins (GPCR) with the fusion partners, as inserted fragments, from mammalian cells. The fusion partners are from a fragment of APJ protein ("the APJ protein fragment") or a fragment with homology of more than 90% similarity to the APJ protein fragment; or a fragment of RGS16 protein (the "RGS16 protein fragment") or a fragment with homology of more than 90% similarity to the RGS16 protein fragment; or the fragment of DNJ protein (the "DNJ protein fragment") or a fragment with homology of more than 90% similarity to DNJ protein fragment. The fusion expression of GPCR with the above mentioned fusion partners can improve the protein yield and stability when purified from cells. Therefore, these fusion protein partners can be widely used for the study of GPCR proteins.

5 Claims, 5 Drawing Sheets

Specification includes a Sequence Listing.

SEQUENCE LISTING

<160> NUMBER OF SEQ ID NOS: 26

<210> SEQ ID NO 1
<211> LENGTH: 104
<212> TYPE: PRT
<213> ORGANISM: Artificial Sequence
<220> FEATURE:
<223> OTHER INFORMATION: APC

<400> SEQUENCE: 1

```
Ser Thr Gly Tyr Leu Glu Glu Leu Glu Lys Glu Arg Ser Leu Leu Leu
1               5                   10                  15

Ala Asp Leu Asp Lys Glu Glu Lys Glu Lys Asp Trp Tyr Tyr Ala Gln
            20                  25                  30

Leu Gln Asn Leu Thr Lys Arg Ile Asp Ser Leu Pro Leu Thr Glu Asn
        35                  40                  45

Phe Ser Leu Gln Thr Asp Met Thr Arg Arg Gln Leu Glu Tyr Glu Ala
    50                  55                  60

Arg Gln Ile Arg Val Ala Met Glu Glu Gln Leu Gly Thr Cys Gln Asp
65                  70                  75                  80

Met Glu Lys Arg Ala Gln Arg Arg Ile Ala Arg Ile Gln Gln Ile Glu
                85                  90                  95

Lys Asp Ile Leu Arg Ile Arg Gln
            100
```

<210> SEQ ID NO 2
<211> LENGTH: 135
<212> TYPE: PRT
<213> ORGANISM: Artificial Sequence
<220> FEATURE:
<223> OTHER INFORMATION: RGS16

<400> SEQUENCE: 2

```
Asn Phe Ser Glu Asp Val Leu Gly Trp Arg Glu Ser Phe Asp Leu Leu
1               5                   10                  15

Leu Ser Ser Lys Asn Gly Val Ala Ala Phe His Ala Phe Leu Lys Thr
            20                  25                  30

Glu Phe Ser Glu Glu Asn Leu Glu Phe Trp Leu Ala Cys Glu Glu Phe
        35                  40                  45

Lys Lys Ile Arg Ser Ala Thr Lys Leu Ala Ser Arg Ala His Gln Ile
    50                  55                  60

Phe Glu Glu Phe Ile Cys Ser Glu Ala Pro Lys Glu Val Asn Ile Asp
65                  70                  75                  80

His Glu Thr His Glu Leu Thr Arg Met Asn Leu Gln Thr Ala Thr Ala
                85                  90                  95

Thr Cys Phe Asp Ala Ala Gln Gly Lys Thr Arg Thr Leu Met Glu Lys
            100                 105                 110

Asp Ser Tyr Pro Arg Phe Leu Lys Ser Pro Ala Tyr Arg Asp Leu Ala
        115                 120                 125

Ala Gln Ala Ser Ala Ala Ser
    130                 135
```

<210> SEQ ID NO 3
<211> LENGTH: 63
<212> TYPE: PRT
<213> ORGANISM: Artificial Sequence
<220> FEATURE:
<223> OTHER INFORMATION: DNJ

<400> SEQUENCE: 3

Gly Tyr Tyr Asp Val Leu Gly Val Lys Pro Asp Ala Ser Asp Asn Glu
1               5                   10                  15

Leu Lys Lys Ala Tyr Arg Lys Met Ala Leu Lys Phe His Pro Asp Lys
                20                  25                  30

Asn Pro Asp Gly Ala Glu Gln Phe Lys Gln Ile Ser Gln Ala Tyr Glu
            35                  40                  45

Val Leu Ser Asp Glu Lys Lys Arg Gln Ile Tyr Asp Gln Gly Gly
    50                  55                  60

<210> SEQ ID NO 4
<211> LENGTH: 312
<212> TYPE: DNA
<213> ORGANISM: Artificial Sequence
<220> FEATURE:
<223> OTHER INFORMATION: APC

<400> SEQUENCE: 4

```
tccaccggct acctggagga gctggagaag gagcgctccc tgctgctggc cgacctggac      60
aaggaggaga aggagaagga ctggtactac gcccagctgc agaacctgac caagcgcatc     120
gactccctgc cctgaccga aacttctcc ctgcagaccg acatgacccg ccgccagctg     180
gagtacgagg cccgccagat ccgcgtggcc atggaggagc agctgggcac ctgccaggac     240
atggagaagc gcgcccagcg ccgcatcgcc cgcatccagc agatcgagaa ggacatcctg     300
cgcatccgcc ag                                                         312
```

<210> SEQ ID NO 5
<211> LENGTH: 405
<212> TYPE: DNA
<213> ORGANISM: Artificial Sequence
<220> FEATURE:
<223> OTHER INFORMATION: RGS16

<400> SEQUENCE: 5

```
aacttctccg aggacgtgct gggctggcgc gagtccttcg acctgctgct gtcctccaag      60
aacggcgtgg ccgccttcca cgccttcctg aagaccgagt ctccgaggga gaacctggag     120
ttctggctgg cctgcgagga gttcaagaag atccgctccg ccaccaagct ggcctcccgc     180
gcccaccaga tcttcgagga gttcatctgc tccgaggccc caaggaggt gaacatcgac      240
cacgagaccc acgagctgac ccgcatgaac ctgcagaccg ccaccgccac ctgcttcgac     300
gccgcccagg gcaagaccc caccctgatg gagaaggact cctaccccg cttcctgaag      360
tccccccgcct accgcgacct ggccgcccag gcctccgccg cctcc                    405
```

<210> SEQ ID NO 6
<211> LENGTH: 189
<212> TYPE: DNA
<213> ORGANISM: Artificial Sequence
<220> FEATURE:
<223> OTHER INFORMATION: DNJ

<400> SEQUENCE: 6

```
ggctactacg acgtgctggg cgtgaagccc gacgcctccg acaacgagct gaagaaggcc      60
taccgcaaga tggccctgaa gttccacccc gacaagaacc ccgacggcgc cgagcagttc     120
aagcagatct cccaggccta cgaggtgctg tccgacgaga agaagcgcca gatctacgac     180
cagggcggc                                                             189
```

<210> SEQ ID NO 7
<211> LENGTH: 427
<212> TYPE: PRT
<213> ORGANISM: Artificial Sequence
<220> FEATURE:
<223> OTHER INFORMATION: A2a-APC

<400> SEQUENCE: 7

```
Asp Tyr Lys Asp Asp Asp Ala Pro Ile Met Gly Ser Ser Val Tyr
1               5                   10                  15

Ile Thr Val Glu Leu Ala Ile Ala Val Leu Ala Ile Leu Gly Asn Val
                20                  25                  30

Leu Val Cys Trp Ala Val Trp Leu Asn Ser Asn Leu Gln Asn Val Thr
            35                  40                  45

Asn Tyr Phe Val Val Ser Leu Ala Ala Ala Asp Ile Ala Val Gly Val
        50                  55                  60

Leu Ala Ile Pro Phe Ala Ile Thr Ile Ser Thr Gly Phe Cys Ala Ala
65                  70                  75                  80

Cys His Gly Cys Leu Phe Ile Ala Cys Phe Val Leu Val Leu Thr Gln
                85                  90                  95

Ser Ser Ile Phe Ser Leu Leu Ala Ile Ala Ile Asp Arg Tyr Ile Ala
            100                 105                 110

Ile Arg Ile Pro Leu Arg Tyr Asn Gly Leu Val Thr Gly Thr Arg Ala
        115                 120                 125

Lys Gly Ile Ile Ala Ile Cys Trp Val Leu Ser Phe Ala Ile Gly Leu
130                 135                 140

Thr Pro Met Leu Gly Trp Asn Asn Cys Gly Gln Pro Lys Glu Gly Lys
145                 150                 155                 160

Asn His Ser Gln Gly Cys Gly Glu Gly Gln Val Ala Cys Leu Phe Glu
                165                 170                 175

Asp Val Val Pro Met Asn Tyr Met Val Tyr Phe Asn Phe Phe Ala Cys
            180                 185                 190

Val Leu Val Pro Leu Leu Leu Met Leu Gly Val Tyr Leu Arg Ile Phe
        195                 200                 205

Leu Ala Ala Arg Arg Gln Leu Ser Thr Gly Tyr Leu Glu Glu Leu Glu
210                 215                 220

Lys Glu Arg Ser Leu Leu Leu Ala Asp Leu Asp Lys Glu Glu Lys Glu
225                 230                 235                 240

Lys Asp Trp Tyr Tyr Ala Gln Leu Gln Asn Leu Thr Lys Arg Ile Asp
                245                 250                 255

Ser Leu Pro Leu Thr Glu Asn Phe Ser Leu Gln Thr Asp Met Thr Arg
            260                 265                 270

Arg Gln Leu Glu Tyr Glu Ala Arg Gln Ile Arg Val Ala Met Glu Glu
        275                 280                 285

Gln Leu Gly Thr Cys Gln Asp Met Glu Lys Arg Ala Gln Arg Arg Ile
290                 295                 300

Ala Arg Ile Gln Gln Ile Glu Lys Asp Ile Leu Arg Ile Arg Gln Glu
305                 310                 315                 320

Arg Ala Arg Ser Thr Leu Gln Lys Glu Val His Ala Ala Lys Ser Leu
                325                 330                 335

Ala Ile Ile Val Gly Leu Phe Ala Leu Cys Trp Leu Pro Leu His Ile
            340                 345                 350

Ile Asn Cys Phe Thr Phe Phe Cys Pro Asp Cys Ser His Ala Pro Leu
        355                 360                 365
```

```
Trp Leu Met Tyr Leu Ala Ile Val Leu Ser His Thr Asn Ser Val Val
        370                 375                 380

Asn Pro Phe Ile Tyr Ala Tyr Arg Ile Arg Glu Phe Arg Gln Thr Phe
385                 390                 395                 400

Arg Lys Ile Ile Arg Ser His Val Leu Arg Gln Gln Glu Pro Phe Lys
                405                 410                 415

Ala His His His His His His His His
            420                 425

<210> SEQ ID NO 8
<211> LENGTH: 474
<212> TYPE: PRT
<213> ORGANISM: Artificial Sequence
<220> FEATURE:
<223> OTHER INFORMATION: A2a-RGS16

<400> SEQUENCE: 8

Asp Tyr Lys Asp Asp Asp Ala Glu Asn Leu Tyr Phe Gln Ser Phe
1               5                   10                  15

Ser Glu Asp Val Leu Gly Trp Arg Glu Ser Phe Asp Leu Leu Leu Ser
                20                  25                  30

Ser Lys Asn Gly Val Ala Ala Phe His Ala Phe Leu Lys Thr Glu Phe
            35                  40                  45

Ser Glu Glu Asn Leu Glu Phe Trp Leu Ala Cys Glu Glu Phe Lys Lys
50                  55                  60

Ile Arg Ser Ala Thr Lys Leu Ala Ser Arg Ala His Gln Ile Phe Glu
65                  70                  75                  80

Glu Phe Ile Cys Ser Glu Ala Pro Lys Glu Val Asn Ile Asp His Glu
                85                  90                  95

Thr His Glu Leu Thr Arg Met Asn Leu Gln Thr Ala Thr Ala Thr Cys
            100                 105                 110

Phe Asp Ala Ala Gln Gly Lys Thr Arg Thr Leu Met Glu Lys Asp Ser
        115                 120                 125

Tyr Pro Arg Phe Leu Lys Ser Pro Ala Tyr Arg Asp Leu Ala Ala Gln
130                 135                 140

Ala Ser Ala Ala Ser Pro Ile Met Gly Ser Ser Val Tyr Ile Thr Val
145                 150                 155                 160

Glu Leu Ala Ile Ala Val Leu Ala Ile Leu Gly Asn Val Leu Val Cys
                165                 170                 175

Trp Ala Val Trp Leu Asn Ser Asn Leu Gln Asn Val Thr Asn Tyr Phe
            180                 185                 190

Val Val Ser Leu Ala Ala Ala Asp Ile Ala Val Gly Val Leu Ala Ile
        195                 200                 205

Pro Phe Ala Ile Thr Ile Ser Thr Gly Phe Cys Ala Ala Cys His Gly
210                 215                 220

Cys Leu Phe Ile Ala Cys Phe Val Leu Val Leu Thr Gln Ser Ser Ile
225                 230                 235                 240

Phe Ser Leu Leu Ala Ile Ala Ile Asp Arg Tyr Ile Ala Ile Arg Ile
                245                 250                 255

Pro Leu Arg Tyr Asn Gly Leu Val Thr Gly Thr Arg Ala Lys Gly Ile
            260                 265                 270

Ile Ala Ile Cys Trp Val Leu Ser Phe Ala Ile Gly Leu Thr Pro Met
        275                 280                 285

Leu Gly Trp Asn Asn Cys Gly Gln Pro Lys Glu Gly Lys Asn His Ser
290                 295                 300
```

```
Gln Gly Cys Gly Glu Gly Gln Val Ala Cys Leu Phe Glu Asp Val Val
305                 310                 315                 320

Pro Met Asn Tyr Met Val Tyr Phe Asn Phe Ala Cys Val Leu Val
                325                 330                 335

Pro Leu Leu Leu Met Leu Gly Val Tyr Leu Arg Ile Phe Leu Ala Ala
                340                 345                 350

Arg Arg Gln Leu Lys Gln Met Glu Ser Gln Pro Leu Pro Gly Glu Arg
            355                 360                 365

Ala Arg Ser Thr Leu Gln Lys Glu Val His Ala Ala Lys Ser Leu Ala
        370                 375                 380

Ile Ile Val Gly Leu Phe Ala Leu Cys Trp Leu Pro Leu His Ile Ile
385                 390                 395                 400

Asn Cys Phe Thr Phe Phe Cys Pro Asp Cys Ser His Ala Pro Leu Trp
                405                 410                 415

Leu Met Tyr Leu Ala Ile Val Leu Ser His Thr Asn Ser Val Val Asn
                420                 425                 430

Pro Phe Ile Tyr Ala Tyr Arg Ile Arg Glu Phe Arg Gln Thr Phe Arg
            435                 440                 445

Lys Ile Ile Arg Ser His Val Leu Arg Gln Gln Glu Pro Phe Lys Ala
        450                 455                 460

His His His His His His His His
465                 470

<210> SEQ ID NO 9
<211> LENGTH: 403
<212> TYPE: PRT
<213> ORGANISM: Artificial Sequence
<220> FEATURE:
<223> OTHER INFORMATION: APC-DNJ

<400> SEQUENCE: 9

Asp Tyr Lys Asp Asp Asp Ala Glu Asn Leu Tyr Phe Gln Ser Gly
1               5                   10                  15

Tyr Tyr Asp Val Leu Gly Val Lys Pro Asp Ala Ser Asp Asn Glu Leu
                20                  25                  30

Lys Lys Ala Tyr Arg Lys Met Ala Leu Lys Phe His Pro Asp Lys Asn
            35                  40                  45

Pro Asp Gly Ala Glu Gln Phe Lys Gln Ile Ser Gln Ala Tyr Glu Val
        50                  55                  60

Leu Ser Asp Glu Lys Lys Arg Gln Ile Tyr Asp Gln Gly Gly Pro Ile
65                  70                  75                  80

Met Gly Ser Ser Val Tyr Ile Thr Val Glu Leu Ala Ile Ala Val Leu
                85                  90                  95

Ala Ile Leu Gly Asn Val Leu Val Cys Trp Ala Val Trp Leu Asn Ser
                100                 105                 110

Asn Leu Gln Asn Val Thr Asn Tyr Phe Val Val Ser Leu Ala Ala Ala
            115                 120                 125

Asp Ile Ala Val Gly Val Leu Ala Ile Pro Phe Ala Ile Thr Ile Ser
        130                 135                 140

Thr Gly Phe Cys Ala Ala Cys His Gly Cys Leu Phe Ile Ala Cys Phe
145                 150                 155                 160

Val Leu Val Leu Thr Gln Ser Ser Ile Phe Ser Leu Leu Ala Ile Ala
                165                 170                 175

Ile Asp Arg Tyr Ile Ala Ile Arg Ile Pro Leu Arg Tyr Asn Gly Leu
            180                 185                 190
```

Val Thr Gly Thr Arg Ala Lys Gly Ile Ile Ala Ile Cys Trp Val Leu
            195                 200                 205

Ser Phe Ala Ile Gly Leu Thr Pro Met Leu Gly Trp Asn Asn Cys Gly
    210                 215                 220

Gln Pro Lys Glu Gly Lys Asn His Ser Gln Gly Cys Gly Glu Gly Gln
225                 230                 235                 240

Val Ala Cys Leu Phe Glu Asp Val Val Pro Met Asn Tyr Met Val Tyr
                245                 250                 255

Phe Asn Phe Phe Ala Cys Val Leu Val Pro Leu Leu Leu Met Leu Gly
            260                 265                 270

Val Tyr Leu Arg Ile Phe Leu Ala Ala Arg Arg Gln Leu Lys Gln Met
        275                 280                 285

Glu Ser Gln Pro Leu Pro Gly Glu Arg Ala Arg Ser Thr Leu Gln Lys
290                 295                 300

Glu Val His Ala Ala Lys Ser Leu Ala Ile Ile Val Gly Leu Phe Ala
305                 310                 315                 320

Leu Cys Trp Leu Pro Leu His Ile Ile Asn Cys Phe Thr Phe Phe Cys
                325                 330                 335

Pro Asp Cys Ser His Ala Pro Leu Trp Leu Met Tyr Leu Ala Ile Val
            340                 345                 350

Leu Ser His Thr Asn Ser Val Val Asn Pro Phe Ile Tyr Ala Tyr Arg
        355                 360                 365

Ile Arg Glu Phe Arg Gln Thr Phe Arg Lys Ile Ile Arg Ser His Val
    370                 375                 380

Leu Arg Gln Gln Glu Pro Phe Lys Ala His His His His His His
385                 390                 395                 400

His His His

<210> SEQ ID NO 10
<211> LENGTH: 1332
<212> TYPE: DNA
<213> ORGANISM: Artificial Sequence
<220> FEATURE:
<223> OTHER INFORMATION: A2a-APC

<400> SEQUENCE: 10
atgaaaacca ttattgcgct gagctatatt ttttgcctgg tgtttgcgga ttataaagat      60
gatgatgatg cgcccatcat gggctcctcg gtgtacatca cggtggagct ggccattgct     120
gtgctggcca tcctgggcaa tgtgctggtg tgctgggccg tgtggctcaa cagcaacctg     180
cagaacgtca ccaactactt tgtggtgtca ctggcggcgg ccgacatcgc agtgggtgtg     240
ctcgccatcc cctttgccat caccatcagc accgggttct gcgctgcctg ccacggctgc     300
ctcttcattg cctgcttcgt cctggtcctc acgcagagct ccatcttcag tctcctggcc     360
atcgccattg accgctacat tgccatccgc atcccgctcc ggtacaatgg cttggtgacc     420
ggcacgaggg ctaagggcat cattgccatc tgctgggtgc tgtcgtttgc catcggcctg     480
actcccatgc taggttggaa caactgcggt cagccaaagg agggcaagaa ccactcccag     540
ggctgcgggg agggccaagt ggcctgtctc tttgaggatg tggtcccat gaactacatg      600 gtgtacttca acttctttgc ctgtgtgctg gtgcccctgc tgctcatgct gggtgtctat     660
ttgcggatct tcctggcggc gcgacgacag ctgtccaccg gctacctgga ggagctggag     720
aaggagcgct ccctgctgct ggccgacctg gacaaggagg agaaggagaa ggactggtac     780
tacgcccagc tgcagaacct gaccaagcgc atcgactccc tgcccctgac cgagaacttc     840

-continued

| | |
|---|---|
| tccctgcaga ccgacatgac ccgccgccag ctggagtacg aggcccgcca gatccgcgtg | 900 |
| gccatggagg agcagctggg cacctgccag gacatggaga agcgcgccca cgcccgcatc | 960 |
| gcccgcatcc agcagatcga aaggacatc ctgcgcatcc gccaggagcg ggcacggtcc | 1020 |
| acactgcaga aggaggtcca tgctgccaag tcactggcca tcattgtggg gctcttttgcc | 1080 |
| ctctgctggc tgcccctaca catcatcaac tgcttcactt tcttctgccc cgactgcagc | 1140 |
| cacgcccctc tctggctcat gtacctggcc atcgtcctct cccacaccaa ttcggttgtg | 1200 |
| aatcccttca tctacgccta ccgtatccgc gagttccgcc agaccttccg caagatcatt | 1260 |
| cgcagccacg tcctgaggca gcaagaacct ttcaaggcac atcatcatca ccatcaccac | 1320 |
| catcaccatt aa | 1332 |

<210> SEQ ID NO 11
<211> LENGTH: 1476
<212> TYPE: DNA
<213> ORGANISM: Artificial Sequence
<220> FEATURE:
<223> OTHER INFORMATION: A2a-RGS16

<400> SEQUENCE: 11

| | |
|---|---|
| atgaaaacca ttattgcgct gagctatatt ttttgcctgg tgtttgcgga ttataaagat | 60 |
| gatgatgatg cggagaacct gtacttccaa tccaacttct ccgaggacgt gctgggctgg | 120 |
| cgcgagtcct tcgacctgct gctgtcctcc aagaacggcg tggccgcctt ccacgccttc | 180 |
| ctgaagaccg agttctccga ggagaacctg gagttctggc tggcctgcga ggagttcaag | 240 |
| aagatccgct ccgccaccaa gctggcctcc cgcgcccacc agatcttcga ggagttcatc | 300 |
| tgctccgagg cccccaagga ggtgaacatc gaccacgaga cccacgagct gacccgcatg | 360 |
| aacctgcaga ccgccaccgc cacctgcttc gacgccgccc agggcaagac ccgcaccctg | 420 |
| atggagaagg actcctaccc ccgcttcctg aagtcccccg cctaccgcga cctggccgcc | 480 |
| caggcctccg ccgcctcccc catcatgggc tcctcggtgt acatcacggt ggagctggcc | 540 |
| attgctgtgc tggccatcct gggcaatgtg ctggtgtgct gggccgtgtg gctcaacagc | 600 |
| aacctgcaga acgtcaccaa ctactttgtg gtgtcactgg cggcggccga catcgcagtg | 660 |
| ggtgtgctcg ccatcccctt tgccatcacc atcagcaccg ggttctgcgc tgcctgccac | 720 |
| ggctgcctct tcattgcctg cttcgtcctg gtcctcacgc agagctccat cttcagtctc | 780 |
| ctggccatcg ccattgaccg ctacattgcc atccgcatcc cgctccggta caatggcttg | 840 |
| gtgaccggca cgagggctaa gggcatcatt gccatctgct gggtgctgtc gtttgccatc | 900 |
| ggcctgactc ccatgctagg ttggaacaac tgccgtcagc caaaggaggg caagaaccac | 960 |
| tcccagggct gcggggaggg ccaagtggcc tgtctctttg aggatgtggt ccccatgaac | 1020 |
| tacatggtgt acttcaactt ctttgcctgt gtgctggtgc cctgctgct catgctgggt | 1080 |
| gtctatttgc ggatcttcct ggcggcgcga cgacagctga agcagatgga gagccagcct | 1140 |
| ctgccggggg agcgggcacg gtccacactg cagaaggagg tccatgctgc caagtcactg | 1200 |
| gccatcattg tggggctctt tgccctctgc tggctgcccc tacacatcat caactgcttc | 1260 |
| actttcttct gccccgactg cagccacgcc cctctctggc tcatgtacct ggccatcgtc | 1320 |
| ctctcccaca ccaattcggt tgtgaatccc ttcatctacg cctaccgtat ccgcgagttc | 1380 |
| cgccagacct tccgcaagat cattcgcagc cacgtcctga ggcagcaaga acctttcaag | 1440 |
| gcacatcatc atcaccatca ccaccatcac cattaa | 1476 |

<210> SEQ ID NO 12
<211> LENGTH: 1260
<212> TYPE: DNA
<213> ORGANISM: Artificial Sequence
<220> FEATURE:
<223> OTHER INFORMATION: A2a-DNJ

<400> SEQUENCE: 12

| | |
|---|---:|
| atgaaaacca ttattgcgct gagctatatt ttttgcctgg tgtttgcgga ttataaagat | 60 |
| gatgatgatg cggagaacct gtacttccaa tccggctact acgacgtgct gggcgtgaag | 120 |
| cccgacgcct ccgacaacga gctgaagaag gcctaccgca agatggccct gaagttccac | 180 |
| cccgacaaga accccgacgg cgccgagcag ttcaagcaga tctcccaggc ctacgaggtg | 240 |
| ctgtccgacg agaagaagcg ccagatctac gaccagggcg cccccatcat gggctcctcg | 300 |
| gtgtacatca cggtggagct ggccattgct gtgctggcca tcctgggcaa tgtgctggtg | 360 |
| tgctgggccg tgtggctcaa cagcaacctg cagaacgtca ccaactactt tgtggtgtca | 420 |
| ctggcggcgg ccgacatcgc agtgggtgtg ctcgccatcc cctttgccat caccatcagc | 480 |
| accgggttct gcgctgcctg ccacggctgc ctcttcattg cctgcttcgt cctggtcctc | 540 |
| acgcagagct ccatcttcag tctcctggcc atcgccattg accgctacat tgccatccgc | 600 |
| atcccgctcc ggtacaatgg cttggtgacc ggcacgaggg ctaagggcat cattgccatc | 660 |
| tgctgggtgc tgtcgtttgc catcggcctg actcccatgc taggttggaa caactgcggt | 720 |
| cagccaaagg agggcaagaa ccactcccag ggctgcgggg agggccaagt ggcctgtctc | 780 |
| tttgaggatg tggtccccat gaactacatg gtgtacttca acttctttgc ctgtgtgctg | 840 |
| gtgccctgc tgctcatgct gggtgtctat ttgcggatct tcctggcggc gcgacgacag | 900 |
| ctgaagcaga tggagagcca gcctctgccg ggggagcggg cacggtccac actgcagaag | 960 |
| gaggtccatg ctgccaagtc actggccatc attgtggggc tctttgccct ctgctggctg | 1020 |
| cccctacaca tcatcaactg cttcacttc ttctgccccg actgcagcca cgcccctctc | 1080 |
| tggctcatgt acctggccat cgtcctctcc cacaccaatt cggttgtgaa tcccttcatc | 1140 |
| tacgcctacc gtatccgcga gttccgccag accttccgca agatcattcg cagccacgtc | 1200 |
| ctgaggcagc aagaaccttt caaggcacat catcatcacc atcaccacca tcaccattaa | 1260 |

<210> SEQ ID NO 13
<211> LENGTH: 43
<212> TYPE: DNA
<213> ORGANISM: Artificial Sequence
<220> FEATURE:
<223> OTHER INFORMATION: Forward primer

<400> SEQUENCE: 13

| | |
|---|---:|
| ttcctggcgg cgcgacgaca gctgtccacc ggctacctgg agg | 43 |

<210> SEQ ID NO 14
<211> LENGTH: 41
<212> TYPE: DNA
<213> ORGANISM: Artificial Sequence
<220> FEATURE:
<223> OTHER INFORMATION: Reverse primer

<400> SEQUENCE: 14

| | |
|---|---:|
| cagtgtggac cgtgcccgct cctggcggat gcgcaggatg t | 41 |

<210> SEQ ID NO 15
<211> LENGTH: 41
<212> TYPE: DNA
<213> ORGANISM: Artificial Sequence
<220> FEATURE:
<223> OTHER INFORMATION: Forward primer

<400> SEQUENCE: 15
gagaacctgt acttccaatc caacttctcc gaggacgtgc t         41

<210> SEQ ID NO 16
<211> LENGTH: 40
<212> TYPE: DNA
<213> ORGANISM: Artificial Sequence
<220> FEATURE:
<223> OTHER INFORMATION: Reverse primer

<400> SEQUENCE: 16
acaccgagga gcccatgatg ggggaggcgg cggaggcctg            40

<210> SEQ ID NO 17
<211> LENGTH: 40
<212> TYPE: DNA
<213> ORGANISM: Artificial Sequence
<220> FEATURE:
<223> OTHER INFORMATION: Forward primer

<400> SEQUENCE: 17
gagaacctgt acttccaatc cggctactac gacgtgctgg            40

<210> SEQ ID NO 18
<211> LENGTH: 41
<212> TYPE: DNA
<213> ORGANISM: Artificial Sequence
<220> FEATURE:
<223> OTHER INFORMATION: Reverse primer

<400> SEQUENCE: 18
acaccgagga gcccatgatg gggccgccct ggtcgtagat c         41

<210> SEQ ID NO 19
<211> LENGTH: 1344
<212> TYPE: DNA
<213> ORGANISM: Artificial Sequence
<220> FEATURE:
<223> OTHER INFORMATION: A2a DNA template

<400> SEQUENCE: 19
atgaaaacca ttattgcgct gagctatatt ttttgcctgg tgtttgcgga ttataaagat     60
gatgatgatg gcgcgccgcc catcatgggc tcctcggtgt acatcacggt ggagctggcc    120
attgctgtgc tggccatcct gggcaatgtg ctggtgtgct gggccgtgtg gctcaacagc    180
aacctgcaga acgtcaccaa ctactttgtg gtgtcactgg cggcggccga catcgcagtg    240
ggtgtgctcg ccatcccctt tgccatcacc atcagcaccg ggttctgcgc tgcctgccac    300
ggctgcctct tcattgcctg cttcgtcctg gtcctcacgc agagctccat cttcagtctc    360
ctggccatcg ccattgaccg ctacattgcc atccgcatcc cgctccggta caatggcttg    420
gtgaccggca cgagggctaa gggcatcatt gccatctgct gggtgctgtc gtttgccatc    480
ggcctgactc ccatgctagg ttggaacaac tgcggtcagc caaggagggc aagaaccac    540 tcccagggct gcggggaggg ccaagtggcc tgtctctttg aggatgtggt ccccatgaac    600
tacatggtgt acttcaactt cttttgcctg tgtgctggtgc ccctgctgct catgctgggt    660

```
gtctatttgc ggatcttcct ggcggcgcga cgacagctgg ctgatctgga agacaattgg    720
gaaactctga acgacaatct caaggtgatc gagaaggctg acaatgctgc acaagtcaaa    780
gacgctctga ccaagatgag ggcagcagcc ctggacgctc agaaggccac tccacctaag    840
ctcgaggaca agagcccaga tagccctgaa atgaaagact ttcggcatgg attcgacatt    900
ctggtgggac agattgatga tgcactcaag ctggccaatg aagggaaagt caaggaagca    960
caagcagccg ctgagcagct gaagaccacc cggaatgcat acattcagaa gtacctggaa   1020
cgtgcacggt ccacactgca gaaggaggtc catgctgcca gtcactggc catcattgtg     1080 gggctctttg ccctctgctg ctgcccccta cacatcatca actgcttcac tttcttctgc   1140
cccgactgca gccacgcccc tctctggctc atgtacctgg ccatcgtcct ctcccacacc   1200
aattcggttg tgaatccctt catctacgcc taccgtatcc gcgagttccg ccagaccttc   1260
cgcaagatca ttcgcagcca cgtcctgagg cagcaagaac ctttcaaggc acatcatcat   1320
caccatcacc accatcacca ttaa                                          1344

<210> SEQ ID NO 20
<211> LENGTH: 68
<212> TYPE: DNA
<213> ORGANISM: Artificial Sequence
<220> FEATURE:
<223> OTHER INFORMATION: Forward primer

<400> SEQUENCE: 20 tatattttt gcctggtgtt tgcggattat aaagatgatg atgatgcgcc catcatgggc      60
tcctcggt                                                             68

<210> SEQ ID NO 21
<211> LENGTH: 36
<212> TYPE: DNA
<213> ORGANISM: Artificial Sequence
<220> FEATURE:
<223> OTHER INFORMATION: Reverse primer

<400> SEQUENCE: 21
cctccaggta gccggtggac agctgtcgtc gcgccg                              36

<210> SEQ ID NO 22
<211> LENGTH: 20
<212> TYPE: DNA
<213> ORGANISM: Artificial Sequence
<220> FEATURE:
<223> OTHER INFORMATION: Forward primer

<400> SEQUENCE: 22
gagcgggcac ggtccacact                                                20

<210> SEQ ID NO 23
<211> LENGTH: 39
<212> TYPE: DNA
<213> ORGANISM: Artificial Sequence
<220> FEATURE:
<223> OTHER INFORMATION: Reverse primer

<400> SEQUENCE: 23
ttaatggtga tggtggtgat ggtgatgatg atgtgccttt                          39

<210> SEQ ID NO 24
<211> LENGTH: 20
<212> TYPE: DNA
<213> ORGANISM: Artificial Sequence
```

```
<220> FEATURE:
<223> OTHER INFORMATION: Forward primer

<400> SEQUENCE: 24
cccatcatgg gctcctcggt                                                      20

<210> SEQ ID NO 25
<211> LENGTH: 59
<212> TYPE: DNA
<213> ORGANISM: Artificial Sequence
<220> FEATURE:
<223> OTHER INFORMATION: Reverse primer

<400> SEQUENCE: 25
ttggtaccgc atgcctcgag ttaatggtga tggtggtgat ggtgatgatg atgtgcctt          59

<210> SEQ ID NO 26
<211> LENGTH: 412
<212> TYPE: PRT
<213> ORGANISM: Artificial Sequence
<220> FEATURE:
<223> OTHER INFORMATION: A2a

<400> SEQUENCE: 26
```

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
        35                  40                  45

Ala Ala Ala Asp Ile Ala Val Gly Val Leu Ala Ile Pro Phe Ala Ile
    50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
        115                 120                 125

Trp Val Leu Ser Phe Ala Ile Gly Leu Thr Pro Met Leu Gly Trp Asn
    130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
        195                 200                 205

Lys Gln Met Glu Ser Gln Pro Leu Pro Gly Glu Arg Ala Arg Ser Thr
    210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270

-continued

```
Ala Ile Val Leu Ser His Thr Asn Ser Val Val Asn Pro Phe Ile Tyr
        275                 280                 285

Ala Tyr Arg Ile Arg Glu Phe Arg Gln Thr Phe Arg Lys Ile Ile Arg
        290                 295                 300

Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
                325                 330                 335

Arg Leu Asn Gly His Pro Pro Gly Val Trp Ala Asn Gly Ser Ala Pro
            340                 345                 350

His Pro Glu Arg Arg Pro Asn Gly Tyr Ala Leu Gly Leu Val Ser Gly
        355                 360                 365

Gly Ser Ala Gln Glu Ser Gln Gly Asn Thr Gly Leu Pro Asp Val Glu
        370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
                405                 410
```

NUCLEIC ACID SEQUENCE ENCODING A FUSION PROTEIN

CROSS-REFERENCE TO RELATED APPLICATION

This application is a divisional of and claims the priority benefit of U.S. application Ser. No. 14/633,153, filed on Feb. 27, 2015, now allowed, which is a continuation-in-part application of PCT application serial no. PCT/CN2014/070537, filed on Jan. 13, 2014, which claims the priority benefit of China application no. 201310577289.9, filed on Nov. 18, 2013. The entirety of each of the above-mentioned patent applications is hereby incorporated by reference herein and made a part of this specification.

BACKGROUND OF THE INVENTION

1. Field of the Invention

This invention relates to genetic engineering and specifically fusion expression of G-protein coupled receptors (GPCRs).

2. Description of Related Art

G-protein coupled receptors (GPCRs) are a large family of transmembrane protein receptors. All GPRCs share a common structural feature, that is, an extracellular N-terminus, followed by seven transmembrane α-helices connected by three intracellular and three extracellular loops and finally an intracellular C-terminus.

The extracellular regions often have glycosylated residues. The C-terminus and the intracellular loop between the fifth and sixth transmembrane helical regions together form the G protein binding site. There are 800 known GPCRs so far, which can be classified into six classes: Class A (or 1) (Rhodopsin-like); Class B (or 2) (Secretin receptor family); Class C (or 3) (Metabotropic glutamate/pheromone); Class D (or 4) (Fungal mating pheromone receptors); Class E (or 5) (Cyclic AMP receptors); and Class F (or 6) (Frizzled/Smoothened). [Friedricksson et al., Mol. Phannacol. 63 (6):1256-1272, 2003: and Friedricksson et al., Mol. Pharmacol. 67 (5):1414-1425, 2005]. There is little nucleotide sequence homology between the GPCRs classes.

By coupling with different G proteins, the various GPCRs react to a vast array of extracellular signals, leading to a series of physiology effects including neural transmission, smell, taste, vision and cellular metabolism, differentiation, reproduction and endocrine responses.

Numerous diseases are known to be associated with GPCRs. More than 40% of modern drugs, and over half of the thousands of drugs on the market target GPCRs. These GPCR-targeting drugs are effective treatments of pain, cognizance impairment, high blood pressure, ulcer, nasal inflammation and asthma. Due to the important physiological roles of GPCRs, their structure and function have been intensively studied.

However, wild type GPCRs are unstable in vitro and it is difficult to obtain pure and stable form. Recently, several research groups reported methods used to improve the stability of GPCRs, including (1) insertion of an E. coli T4 phage lysozyme T4L between the ICL3 (intracellular loop 3) and the N-terminus. This approach has been successfully applied to the studies of A2a receptor, CXCR4 receptor, beta-2 adrenergic receptor, D3 dopamine receptor, S1P1 receptor etc. The modification of GPCR with T4L has led to high expression and high yield, and eventually to a high-resolution crystal structure. [Rasmussen et al., Crystal structure of the human beta2 adrenergic G-protein-coupled receptor, Nature 450: 383-387, 2007; Wu et al., Structures of the CXCR4 chemokine GPCR with small-molecule and cyclic peptide antagonists Science 330: 1066-1071, 2010; Chien et al., Structure of the human dopamine D3 receptor in complex with a D2/D3 selective antagonist, Science 330: 1091-1095, 2010; Xu et al., Structure of an agonist-bound human A2A adenosine receptor, Science 332: 322-327, 2011; Hanson et al., Crystal structure of a lipid G protein-coupled receptor; Science 335: 851-855, 2012; and Zou et al., N-terminal T4 lysozyme fusion facilitates crystallization of a G protein coupled receptor Plos One 7: e46039-e46039 2012]. (2) Insertion of bacterial Bril protein in the N-terminus or ICL3. This has been successfully applied to GPCRs such as adenosine A2a receptor, Nociceptin/orphanin FQ receptor, 5HT1b, 5HT2b and SMO receptor, leading to successful determination of their crystal structures. [Liu, W. et al. Structural basis for allosteric regulation of GPCRs by sodium ions, Science 337: 232-236, 2012. Thompson, A. A. et al. Structure of the nociceptiniorphanin FQ receptor in complex with a peptide mimetic Nature 485: 395-399, 2012. Wang, C. et al. Structural Basis for Molecular Recognition at Serotonin Receptors Science 2013. Wang, C. Structure of the human smoothened 7TM receptor in complex with an antitumor agent Nature 2013]. (3) Mutation screening of GPCRs for mutants which possess improved stability with unaffected protein structure and function. This approach has been successfully demonstrated the stable preparation of A2a and beta-1 adrenergic receptor with high yield and high resolution crystal structures [Lebon, G. et al. Agonist-bound adenosine A2A receptor structures reveal common features of GPCR activation. Nature 474: 521, 2011. Warne, A. et al. Structure of a betal-adrenergic G-protein-coupled receptor Nature 454: 486, 2008]. (4) Using antibody to stabilize the configuration of GPCRs. Using this approach, the Brian Kobilka Laboratory of Stanford University obtained a high resolution crystal structure of beta-2 adrenergic receptor [Bokoch M. P. et al., Ligand-specific regulation of the extracellular surface of a G-protein-coupled receptor, Nature 463: 108-112, 2010].

So far, all proteins used as fusion partners to stabilize GPCRs are prokaryotic proteins, and there has been no report of using a eukaryotic fusion protein partner. Use of eukaryotic fusion protein partners for GPCR protein expression may be advantageous since all GPCRs are present in eukaryotic cells. Therefore it would be desirable to find eukaryotic protein partners for GPCRs fusion expression. Furthermore, even though T4L and Bril proteins have successfully been applied to some GPCRs for expression and purification, they are not useful for many other GPCRs. Thus, additional fusion protein partners are highly desirable.

SUMMARY OF THE INVENTION

In some embodiments, the present invention provides a number of novel fusion protein partners as inserted fragments which can be used for expression of GPCRs so as to provide more options for GPCR expression.

Specifically, this invention provides eukaryotic fusion proteins for GPCR expression, i.e. APC, RGS16 and DNJ protein fragments, and demonstrates the successful use of these protein fragments in fusion expression of GPCR proteins.

The fusion protein partners for GPCR expression according to the present invention are characterized by: being from a eukaryotic source, and selected from a fragment of APC protein (the "APC protein fragment") or a polypeptide having greater than 90% amino acid sequence identity to the APC protein fragment; a fragment of RCS16 protein (the "RCS16 protein fragment") or a polypeptide having greater than 90% amino acid sequence identity to the RCS16 protein fragment; or a fragment of DNJ protein (the "DNJ protein fragment") or a polypeptide having greater than 90% amino acid sequence identity to the DNJ protein fragment.

The APC protein fragment has an amino acid sequence as shown in SEQ ID NO:1, which is encoded by a DNA fragment having a nucleic acid sequence as shown in SEQ ID NO: 4; The RCS16 protein fragment has an amino acid sequence as shown in SEQ ID NO:2, which is encoded by a DNA fragment having a nucleic acid sequence as shown in SEQ ID NO:5.

The DNJ protein fragment has an amino acid sequence as shown in SEQ ID NO:3, which is encoded by a DNA fragment having a nucleic acid sequence as shown in SEQ NO: 6.

This invention involves the engineering of GPCR at the N-terminus, C-terminus or ICL3 region through the insertion of the APC, RGS16, or DNJ protein fragment to stabilize GPCR proteins.

In one embodiment, these three protein fragments are used for fusion expression of the A2a protein. When using the APC fragment, the resultant fusion protein comprises an amino acid sequence shown in SEQ ID NO: 7, which is encoded by a DNA fragment having a nucleic acid sequence as shown in SEQ ID NO: 10; when using the RGS16 fragment, the resultant fusion protein comprises an amino acid sequence shown in SEQ ID NO: 8, which is encoded by a DNA fragment having a nucleic acid sequence as shown in SEQ ID NO: 11; and when using the DNJ fragment, the resultant fusion protein comprises an amino acid sequence shown in SEQ ID NO: 9, which is encoded by a DNA fragment having a nucleic acid sequence as shown in SEQ ID NO: 12. Amino acid sequences as shown in SEQ ID NOs: 7, 8 and 9 can be used for fusion expression of the A2a protein; wherein polynucleotides having a nucleotide sequence as shown in SEQ ID NO: 10, 11, or 12 can be introduced into plasmids, such as pFastBac1 (available from Life Technologies), PcDNA3.1 and PET21b for fusion expression of the A2a protein.

It is noted that a person ordinarily skilled in the art can construct a GPCR fusion expression vector comprising the APC, RGS16 or DNJ protein fragment, by using methods well known in the art, such as in vitro recombinant DNA techniques, DNA synthesis techniques, in vivo recombinant techniques. The GPCR fusion expression vector should for example comprise an appropriate promoter which controls mRNA synthesis.

Furthermore, the above constructed vector can be used to transfect or transform appropriate host cells by known methods in the art for culturing and harvest of the expressed protein. For example, using the Bac-to-Bac technique, SF9 cells can be transfected with the fusion expression vector comprising the PFastBac plasmid (see below).

The constructed fusion proteins of the present invention can be expressed in insect cells such as SF9, SF21 and Hive5 and also can be expressed in yeast and mammalian host cells such as 293 or CHO, to produce proteins with a wide variety of applications.

This invention provides mammalian fusion partners, as inserted fragments, for fusion expression of the GPCR: APC, RGS16 and DNJ and further provides the amino acid and DNA sequences of the fusion proteins.

Furthermore, this invention demonstrated application of the above mentioned novel fusion protein partners in the expression of the GPCR, i.e. the A2a receptor. The above mentioned. APC, RGS16 and DNJ protein fragments are inserted into the various regions of A2a (N-terminus, C-terminus or ICL3) and the related amino acid and gene sequences are provided. As a result, the expression yield and in vitro stability of the A2a receptor are greatly improved. These novel fusion proteins can be widely used in the studies of GPCR. The constructs of fusion expression of A2a receptor are provided along with the method of expression in baculo SF9 cell.

DESCRIPTION OF THE EMBODIMENTS

EXAMPLE 1

Figure 1A:
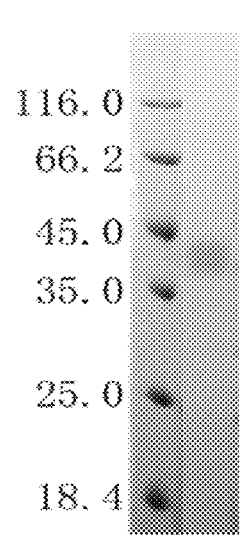
FIG. 1a: SDS gel analysis of A2a-APC fusion protein.

Preparation of Genes Coding for the Fusion Proteins (1) (a) The APC protein fragment comprises an amino acid sequence of SEQ ID NO: 1; and its coding DNA sequence is shown in SEQ ID NO: 4.

```
                                            (SEQ ID NO: 4)
5'-TCCACCGGCTACCTGGAGGAGCTGGAGAAGGAGCGCTCCCTGCTGCT

GGCCGACCTGGACAAGGAGGAGAAGGAGAAGGACTGGTACTACGCCCAGC

TGCAGAACCTGACCAAGCGCATCGACTCCCTGCCCCTGACCGAGAACTTC

TCCCTGCAGACCGACATGACCCGCCGCCAGCTGGAGTACGAGGCCCGCCA

GATCCGCGTGGCCATGGAGGAGCAGCTGGGCACCTGCCAGGACATGGAGA

AGCGCGCCCAGCGCCGCATCGCCCGCATCCAGCAGATCGAGAAGGACATC

CTGCGCATCCGCCAG-3'

Forward primer:
                                            (SEQ ID NO: 13)
5'-TTCCTGGCGGCGCGACGACAGCTGTCCACCGGCTACCTGGAGG-3'

Reverse primer:
                                            (SEQ ID NO: 14)
5'-CAGTGTGGACCGTGCCCGCTCCTGGCGGATGCGCAGGATGT-3'
```

The APC coding sequence was obtained by PCR.
(b) A2a DNA template was chemically synthesized based on human codon usage preference:

```
                                            (SEQ ID NO: 19)
5'-ATGAAAACCATTATTGCGCTGAGCTATATTTTTTGCCTGGTGTTTGC

GGATTATAAAGATGATGATGATGGCGCGCCGCCCATCATGGGCTCCTCGG

TGTACATCACGGTGGAGCTGGCCATTGCTGTGCTGGCCATCCTGGGCAAT
```

-continued
```
GTGCTGGTGTGCTGGGCCGTGTGGCTCAACAGCAACCTGCAGAACGTCAC
CAACTACTTTGTGGTGTCACTGGCGGCGGCCGACATCGCAGTGGGTGTGC
TCGCCATCCCCTTTGCCATCACCATCAGCACCGGGTTCTGCGCTGCCTGC
CACGGCTGCCTCTTCATTGCCTGCTTCGTCCTGGTCCTCACGCAGAGCTC
CATCTTCAGTCTCCTGGCCATCGCCATTGACCGCTACATTGCCATCCGCA
TCCCGCTCCGGTACAATGGCTTGGTGACCGGCACGAGGGCTAAGGGCATC
ATTGCCATCTGCTGGGTGCTGTCGTTTGCCATCGGCCTGACTCCCATGCT
AGGTTGGAACAACTGCGGTCAGCCAAAGGAGGGCAAGAACCACTCCCAGG
GCTGCGGGGAGGGCCAAGTGGCCTGTCTCTTTGAGGATGTGGTCCCCATG
AACTACATGGTGTACTTCAACTTCTTTGCCTGTGTGCTGGTGCCCCTGCT
GCTCATGCTGGGTGTCTATTTGCGGATCTTCCTGGCGGCGCGACGACAGC
TGGCTGATCTGGAAGACAATTGGGAAACTCTGAACGACAATCTCAAGGTG
ATCGAGAAGGCTGACAATGCTGCACAAGTCAAAGACGCTCTGACCAAGAT
GAGGGCAGCAGCCCTGGACGCTCAGAAGGCCACTCCACCTAAGCTCGAGG
ACAAGAGCCCAGATAGCCCTGAAATGAAAGACTTTCGGCATGGATTCGAC
ATTCTGGTGGGACAGATTGATGATGCACTCAAGCTGGCCAATGAAGGGAA
AGTCAAGGAAGCACAAGCAGCCGCTGAGCAGCTGAAGACCACCCGGAATG
CATACATTCAGAAGTACCTGGAACGTGCACGGTCCACACTGCAGAAGGAG
GTCCATGCTGCCAAGTCACTGGCCATCATTGTGGGGCTCTTTGCCCTCTG
CTGGCTGCCCCTACACATCATCAACTGCTTCACTTTCTTCTGCCCCGACT
GCAGCCACGCCCTCTCTGGCTCATGTACCTGGCCATCGTCCTCTCCCAC
ACCAATTCGGTTGTGAATCCCTTCATCTACGCCTACCGTATCCGCGAGTT
CCGCCAGACCTTCCGCAAGATCATTCGCAGCCACGTCCTGAGGCAGCAAG
AACCTTTCAAGGCACATCATCATCACCATCACCACCATCACCATTAA-3'
```
Forward primer
```
                                          (SEQ ID NO: 20)
5'-TATATTTTTTGCCTGGTGTTTGCGGATTATAAAGATGATGATGATGC
GCCCATCATGGGCTCCTCGGT-3'
```
Reverse primer
```
                                          (SEQ ID NO: 21)
5'-CCTCCAGGTAGCCGGTGGACAGCTGTCGTCGCGCCG-3'
```

Using the above template and primers, the coding sequence for A2a (2-208) was obtained by PCR.

Forward primer:
```
                                          (SEQ ID NO: 22)
5'-GAGCGGGCACGGTCCACACT-3'
```
Reverse primer:
```
                                          (SEQ ID NO: 23)
5'-TTAATGGTGATGGTGGTGATGGTGATGATGATGTGCCTT-3'
```

Using the template and the primers above, the coding sequence for A2a (SEQ ID NO: 26, position 219-316) was obtained by PCR.

The coding sequence for A2a (SEQ ID NO: 26, position 2-208)-APC (SEQ ID NO: 1, position 1-104)-A2a (SEQ ID NO: 26, position 219-316) was prepared based on the protocol above. The restriction enzyme site EcoRI was introduced to the forward primer, while the XhoI site and the stop codon were introduced to the reverse primer.

(2) (a) The RGS16 protein fragment comprises an amino acid sequence of SEQ ID NO:2; and its DNA coding sequence is shown as SEQ ID NO:5.

```
                                          (SEQ ID NO: 5)
5'-AACTTCTCCGAGGACGTGCTGGGCTGGCGCGAGTCCTTCGACCTGCT
GCTGTCCTCCAAGAACGGCGTGGCCGCCTTCCACGCCTTCCTGAAGACCG
AGTTCTCCGAGGAGAACCTGGAGTTCTGGCTGGCCTGCGAGGAGTTCAAG
AAGATCCGCTCCGCCACCAAGCTGGCCTCCCGCGCCCACCAGATCTTCGA
GGAGTTCATCTGCTCCGAGGCCCCCAAGGAGGTGAACATCGACCACGAGA
CCCACGAGCTGACCCGCATGAACCTGCAGACCGCCACCGCCACCTGCTTC
GACGCCGCCCAGGGCAAGACCCGCACCCTGATGGAGAAGGACTCCTACCC
CCGCTTCCTGAAGTCCCCCGCCTACCGCGACCTGGCCGCCCAGGCCTCCG
CCGCCTCC-3'
```
Forward primer:
```
                                          (SEQ ID NO: 15)
5'-GAGAACCTGTACTTCCAATCCAACTTCTCCGAGGACGTGCT-3'
```
Reverse primer:
```
                                          (SEQ ID NO: 16)
5'-ACACCGAGGAGCCCATGATGGGGAGGCGGCGGAGGCCTG-3'
```

The RGS16 coding gene was obtained by PCR.

(b) A2a DNA template was chemically synthesized based on human codon usage preference:

```
                                          (SEQ ID NO: 19)
5'-ATGAAAACCATTATTGCGCTGAGCTATATTTTTTGCCTGGTGTTTGC
GGATTATAAAGATGATGATGATGGCGCGCCGCCCATCATGGGCTCCTCGG
TGTACATCACGGTGGAGCTGGCCATTGCTGTGCTGGCCATCCTGGGCAAT
GTGCTGGTGTGCTGGGCCGTGTGGCTCAACAGCAACCTGCAGAACGTCAC
CAACTACTTTGTGGTGTCACTGGCGGCGGCCGACATCGCAGTGGGTGTGC
TCGCCATCCCCTTTGCCATCACCATCAGCACCGGGTTCTGCGCTGCCTGC
CACGGCTGCCTCTTCATTGCCTGCTTCGTCCTGGTCCTCACGCAGAGCTC
CATCTTCAGTCTCCTGGCCATCGCCATTGACCGCTACATTGCCATCCGCA
TCCCGCTCCGGTACAATGGCTTGGTGACCGGCACGAGGGCTAAGGGCATC
ATTGCCATCTGCTGGGTGCTGTCGTTTGCCATCGGCCTGACTCCCATGCT
AGGTTGGAACAACTGCGGTCAGCCAAAGGAGGGCAAGAACCACTCCCAGG
GCTGCGGGGAGGGCCAAGTGGCCTGTCTCTTTGAGGATGTGGTCCCCATG
AACTACATGGTGTACTTCAACTTCTTTGCCTGTGTGCTGGTGCCCCTGCT
GCTCATGCTGGGTGTCTATTTGCGGATCTTCCTGGCGGCGCGACGACAGC
TGGCTGATCTGGAAGACAATTGGGAAACTCTGAACGACAATCTCAAGGTG
ATCGAGAAGGCTGACAATGCTGCACAAGTCAAAGACGCTCTGACCAAGAT
GAGGGCAGCAGCCCTGGACGCTCAGAAGGCCACTCCACCTAAGCTCGAGG
ACAAGAGCCCAGATAGCCCTGAAATGAAAGACTTTCGGCATGGATTCGAC
ATTCTGGTGGGACAGATTGATGATGCACTCAAGCTGGCCAATGAAGGGAA
AGTCAAGGAAGCACAAGCAGCCGCTGAGCAGCTGAAGACCACCCGGAATG
CATACATTCAGAAGTACCTGGAACGTGCACGGTCCACACTGCAGAAGGAG
```

```
GTCCATGCTGCCAAGTCACTGGCCATCATTGTGGGGCTCTTTGCCCTCTG

CTGGCTGCCCCTACACATCATCAACTGCTTCACTTTCTTCTGCCCCGACT

GCAGCCACGCCCCTCTCTGGCTCATGTACCTGGCCATCGTCCTCTCCCAC

ACCAATTCGGTTGTGAATCCCTTCATCTACGCCTACCGTATCCGCGAGTT

CCGCCAGACCTTCCGCAAGATCATTCGCAGCCACGTCCTGAGGCAGAAG

AACCTTTCAAGGCACATCATCATCACCATCACCACCATCACCATTAA-3'

Forward primer
                                              (SEQ ID NO: 24)
5'-CCCATCATGGGCTCCTCGGT-3'

Reverse primer
                                              (SEQ ID NO: 25)
5'-TTGGTACCGCATGCCTCGAGTTAATGGTGATGGTGGTGATGGTGATG

ATGATGTGCCTT-3'
```

Using the template and the primers above, the coding sequence for A2a (219-316) was obtained by PCR.

The coding sequence for RGS16 (SEQ ID NO: 2, position 2-135)-A2a (SEQ ID NO: 26, position 2-316) was prepared based on the protocol above. The restriction enzyme site EcoRI was introduced to the forward primer, while the XhoI site and the stop codon were introduced to the reverse primer.

(3) (a) The DNJ protein fragment comprises an amino acid sequence of SEQ ID NO: 3; and its coding DNA sequence is shown in SEQ ID NO: 6.

```
                                              (SEQ ID NO: 6)
5'-GGCTACTACGACGTGCTGGGCGTGAAGCCCGACGCCTCCGACAACGA

GCTGAAGAAGGCCTACCGCAAGATGGCCCTGAAGTTCCACCCCGACAAGA

ACCCCGACGGCGCCGAGCAGTTCAAGCAGATCTCCCAGGCCTACGAGGTG

CTGTCCGACGAGAAGAAGCGCCAGATCTACGACCAGGGCGGC-3'

Forward primer:
                                              (SEQ ID NO: 17)
5'-GAGAACCTGTACTTCCAATCCGGCTACTACGACGTGCTGG-3'

Reverse primer:
                                              (SEQ ID NO: 18)
5'-ACACCGAGGAGCCCATGATGGGGCCGCCCTGGTCGTAGATC-3'
```

The DNJ coding sequence was obtained by PCR.

(b) A2a DNA template was chemically synthesized based on human codon usage preference:

```
                                              (SEQ ID NO: 19)
5'-ATGAAAACCATTATTGCGCTGAGCTATATTTTTTGCCTGGTGTTTGC

GGATTATAAAGATGATGATGATGGCGCGCCGCCCATCATGGGCTCCTCGG

TGTACATCACGGTGGAGCTGGCCATTGCTGTGCTGGCCATCCTGGGCAAT

GTGCTGGTGTGCTGGGCCGTGTGGCTCAACAGCAACCTGCAGAACGTCAC

CAACTACTTTGTGGTGTCACTGGCGGCGGCCGACATCGCAGTGGGTGTGC

TCGCCATCCCCTTTGCCATCACCATCAGCACCGGGTTCTGCGCTGCCTGC

CACGGCTGCCTCTTCATTGCCTGCTTCGTCCTGGTCCTCACGCAGAGCTC

CATCTTCAGTCTCCTGGCCATCGCCATTGACCGCTACATTGCCATCCGCA

TCCCGCTCCGGTACAATGGCTTGGTGACCGGCACGAGGGCTAAGGGCATC

ATTGCCATCTGCTGGGTGCTGTCGTTTGCCATCGGCCTGACTCCCATGCT
```

```
AGGTTGGAACAACTGCGGTCAGCCAAAGGAGGGCAAGAACCACTCCCAGG

GCTGCGGGGAGGGCCAAGTGGCCTGTCTCTTTGAGGATGTGGTCCCCATG

AACTACATGGTGTACTTCAACTTCTTTGCCTGTGTGCTGGTGCCCCTGCT

GCTCATGCTGGGTGTCTATTTGCGGATCTTCCTGGCGGCGCGACGACAGC

TGGCTGATCTGGAAGACAATTGGGAAACTCTGAACGACAATCTCAAGGTG

ATCGAGAAGGCTGACAATGCTGCACAAGTCAAAGACGCTCTGACCAAGAT

GAGGGCAGCAGCCCTGGACGCTCAGAAGGCCACTCCACCTAAGCTCGAGG

ACAAGAGCCCAGATAGCCCTGAAATGAAAGACTTTCGGCATGGATTCGAC

ATTCTGGTGGGACAGATTGATGATGCACTCAAGCTGGCCAATGAAGGGAA

AGTCAAGGAAGCACAAGCAGCCGCTGAGCAGCTGAAGACCACCCGGAATG

CATACATTCAGAAGTACCTGGAACGTGCACGGTCCACACTGCAGAAGGAG

GTCCATGCTGCCAAGTCACTGGCCATCATTGTGGGGCTCTTTGCCCTCTG

CTGGCTGCCCCTACACATCATCAACTGCTTCACTTTCTTCTGCCCCGACT

GCAGCCACGCCCCTCTCTGGCTCATGTACCTGGCCATCGTCCTCTCCCAC

ACCAATTCGGTTGTGAATCCCTTCATCTACGCCTACCGTATCCGCGAGTT

CCGCCAGACCTTCCGCAAGATCATTCGCAGCCACGTCCTGAGGCAGAAG

AACCTTTCAAGGCACATCATCATCACCATCACCACCATCACCATTAA-3'

Forward primer
                                              (SEQ ID NO: 24)
5'-CCCATCATGGGCTCCTCGGT-3'

Reverse primer
                                              (SEQ ID NO: 25)
5'-TTGGTACCGCATGCCTCGAGTTAATGGTGATGGTGGTGATGGTGATG

ATGATGTGCCTT-3'
```

Using the template and the primers above, the coding sequence for A2a (219-316) was obtained by PCR.

The coding sequence for DNJ (SEQ ID NO: 3, position 1-63)-A2a(SEQ ID NO: 26, position 2-316) was prepared based on the protocol above. The restriction enzyme site EcoRI was introduced to the forward primer, while the XhoI site and the stop codon were introduced to the reverse primer.

PCR was conducted under the following conditions: 0.2 μM each of PCR primer was added into a 50 μl reaction system containing PCR buffer, 1.5 mM $MgSO_4$, 200 μM dNTPs. After mixing thoroughly, a PCR cycle was run on a PCR cycler: denaturation at 94° C. for 5 minutes, denaturation at 94° C. for 30 seconds, annealing at 55° C. for 30 seconds, extending at 68° C. for 2 minutes. This cycle was repeated for 30 times. Finally, the temperature was kept at 68° C. for 10 minutes. PCR product was validated by 1.2% agarose gel electrophoresis, and purified for the purpose of subcloning.

EXAMPLE 2

Construction for the Fusion Protein Plasmid

PCR product from Example 1 and vector pFastBac1 (available from Life Technologies, with brand Invitrogen) were digested by restriction enzymes EcoRI and XhoI, and ligated together. The ligation product was then transformed into competent cells DH5a. The ligation product volume was not higher than 10% of the competent cells volume. The mixture was gently mixed, then incubated in ice for 30 minutes, followed by incubation at 42° C. and heat shock for 60 seconds, and transferred quickly onto ice for 120 seconds to cool down the cells. 400 µl LB medium was then added to the cells. After gently mixed, the cells were recovered and the plasmid-encoded antibiotic marker gene was expressed in a 37° C. shaker for 60 minutes at low speed. Then the cells was spun down by centrifuge at low speed for 2 minutes, kept with about 100 µl LB medium in the tube and the extra supernatant removed. The cells was then re-suspended in 100 µl medium, and plated on a 1.5% agar plate containing 100 µg/ml Ampicilin. The plate was then incubated at 37° C. overnight for 12-16 hours and colonies appeared. The clones were validated by DNA sequencing.

EXAMPLE 3

Expression of the Fusion Proteins

2 µl (>100 ng/µl) of recombinant pFastBac plasmid from Example 2 was added into 100 µl DH10Bac E. coli competent cells. The recombinant pFastBac plasmid volume was not higher than 5% of the competent cells volume. The mixture was gently mixed, then incubated in ice for 30 minutes, followed by incubation at 42° C. and heat shock for 90 seconds, and transferred quickly onto ice for 120 seconds to cool down the cells. 800 µl LB medium was then added to the cells. After gently mixed, the cells was recovered and the plasmid-encoded antibiotic marker gene was expressed was expressed in a 37° C. shaker for 4 hours at low speed (at 250 rpm). 30 µl cells was plated on LB agar plates containing 50 µl/ml Kanamycin, 7 µg/ml Gentmicin, 10 µg/ml tetracycline, 100 µg/ml X-gal and 40 µg/ml IPTG. The plate was then incubated at 37° C. for 30-48 hours and blue and white colonies appeared. The white colonies were selected from the plates and inoculated into 5 ml fresh LB medium containing 50 µl/ml Kanamycin, 7 µg/ml Gentamicin, and 10 µg/ml tetracycline at 37° C. overnight. The cells were validated by PCR analysis. The PCR analysis indicated that the positive cells contained rBacmids. The rBacmids were transfected into SF9 cells with transfection reagent at 27° C. and incubated for 4-5 days and then the culture medium was collected as P1 virus. The sf9 cells were infected with lower MOI (0.01-0.1) with the P1 virus for 72 hours to get P2 virus, used for expression of target peptides. The SF9 cells with density of 2.0×10^6/ml were infected with the P2 virus with infection ratio of 1:100 (Volume/Volume) for 72 hours. The cells were harvested by 4° C. centrifugation at 1500 rpm for 5 minutes, spun down by centrifuge and then washed once with 0.01M PBS buffer.

EXAMPLE 4

Purification of the Fusion Proteins

Insect cell pastes from 1 L cell culture were disrupted by thawing frozen cell pellets in 200 ml hypotonic buffer containing 10 mM HEPES (pH 7.5), 10 mM $MgCl_2$, 20 mM KCl and protease inhibitor cocktail, and then homogenized in ice by a homogenizer. After the homogenization, extensive washing of the isolated raw membranes was performed by repeated centrifugation in the same hypotonic buffer for 3 times, and then in a high osmotic buffer containing 1.0 M NaCl, 10 mM HEPES (pH 7.5), 10 mM $MgCl_2$, 20 mM KCl for 3 times, followed by Dounce homogenization to re-suspend the membranes in 10 mM HEPES (pH 7.5), 10 mM $MgCl_2$, 20 mM KCl, and 40% glycerol, and then flash-frozened with liquid nitrogen and stored at −80° C. until further use.

Purified membranes were thawed in ice in the presence of 4 mM theophylline, 2 mg/mL iodoacetamide. Membranes from 1 L cell culture were disrupted in 100 ml buffer, after incubation for 30 min at 4° C. The membranes were solubilized by incubation in the presence of 0.5% (w/v) DDM and 0.1% (w/v) cholesteryl hemisuccinate for 3 hours at 4° C. The unsolubilized material was removed by centrifugation at 160,000 g for 40 min.

Figure 1B:
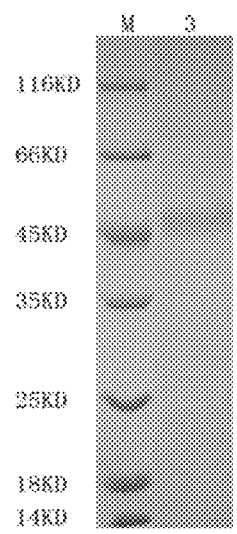
FIG. 1b: SDS gel analysis of A2a-RGS16 fusion protein.
Figure 1C:
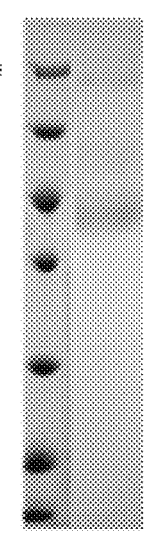
FIG. 1c: SDS gel analysis of A2a-DNJ fusion protein.

The supernatant was incubated with 1 ml pre-equilibrated TALON MAC resin. After overnight binding, the resin was transferred into a gravity column, washed in turn with ten column volumes of 25 mM HEPES (pH 7.5), 800 mM NaCl, 10% (v/v) glycerol, 0.05% (w/v) DDM, 0.001% (w/v) CHS, 25mM Imid, 10 mM $MgCl_2$, 8 mM ATP, followed by four column volumes of 50 mM HEPES (pH 7.5), 800 mM NaCl, 10% (v/v) glycerol, 50 mM imidazole, 0.05% (w/v) DDM, 0.01% (w/v) CHS. The receptor was eluted with 25 mM HEPES (pH 7.5), 800 mM NaCl, 10% (v/v) glycerol, 220 mM imidazole, 0.025% (w/v) DDM, 0.005% (w/v) CHS. Purified receptor was saved at −80° C. FIG. 1 shows SDS gel analysis of three fusion proteins.

All three fusion GPCR proteins have a high yield more than 1 mg/L.

EXAMPLE 5

Thermal Stability of the Fusion Proteins

Prior to use, the dye stock was diluted 1:40 in dye dilution butler and incubated for 5 min at room temperature. 130 µl protein solution was pipetted, 0.13 µl diluted dye was added and mixed together. After 5 min incubation at room temperature, the reaction mixture was transferred to a sub-micro quartz fluorometer cuvette and heated in a controlled way with a ramp rate of 2° C./min in a Cary Eclipse spectrofluorometer. The excitation wavelength was at 387 nm and the grating gap was 2.5 nm, while the emission wavelength was 463 nm and the grating gap was 5 nm. Assays were performed at a temperature ranging from 20° C. to 90° C. and the temperature was increased by 1° C. every minute. All data were processed with GraphPad Prism program and thermal stability value (Tm value) was calculated.

Figure 2A:
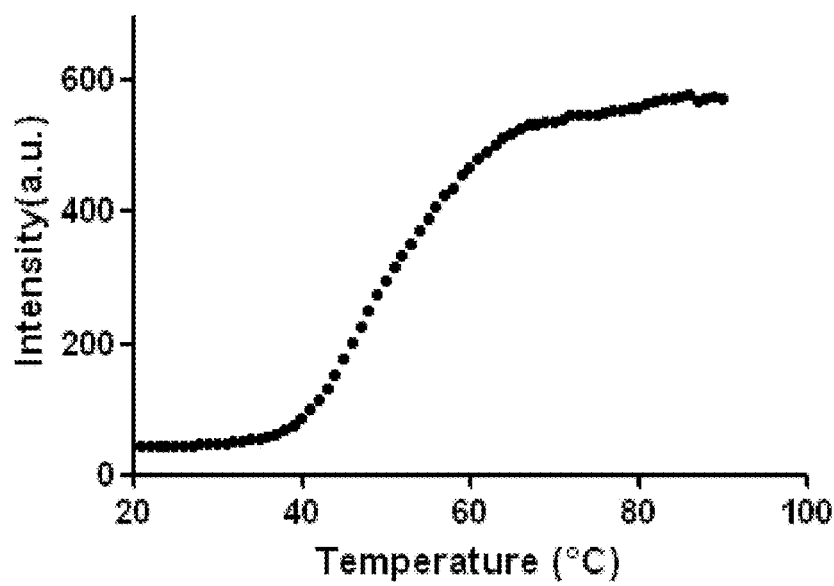
FIG. 2a: Thermal stability measurement of A2a-APC fusion protein in the presence of substrate Adenosine.
Figure 2B:
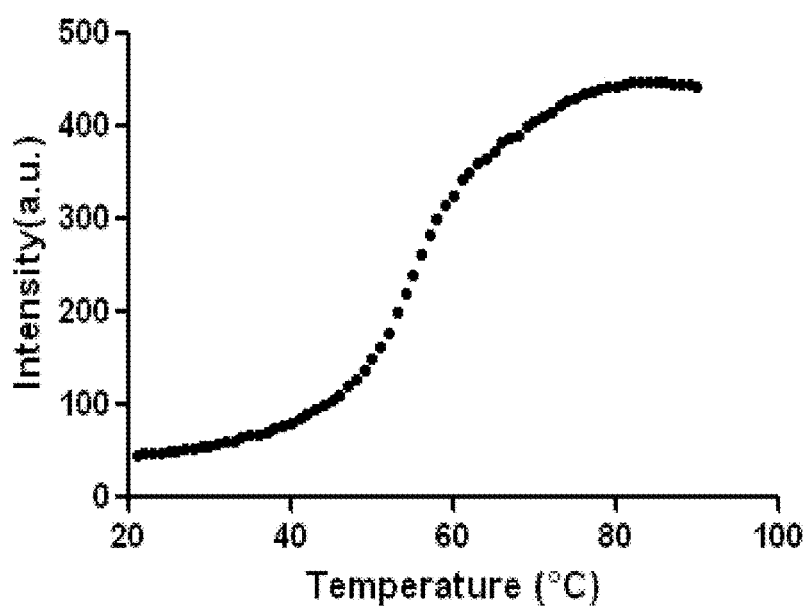
FIG. 2b: Thermal stability measurement of A2a-RGS 16 fusion protein in the presence of substrate Adenosine.
Figure 2C:
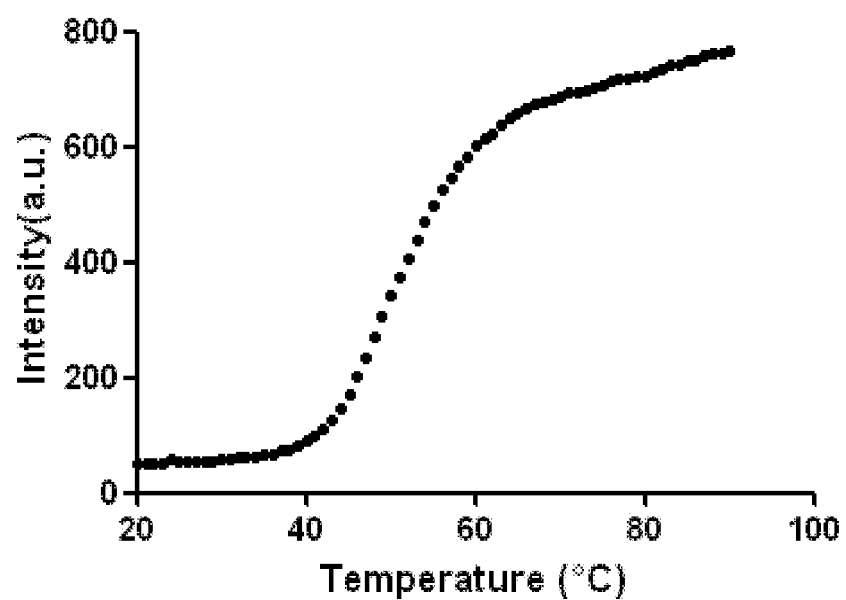
FIG. 2c: Thermal stability measurement of A2a-DNJ fusion protein in the presence of adenosine.

Following above procedure, the Tm value of all three fusion proteins were measured, as showed in FIG. 2.

The Tm value of A2a-APC, A2a-RGS16, A2a-DNJ were 50.8° C., 55.6° C. and 52° C. respectively. All Tm values were higher than 50° C., demonstrating that these fusion proteins have good thermal stability.

EXAMPLE 6

Test of Fusion Protein Homogeneity

Detection was performed by Acquity H-Class Bio UPLC system from Waters, with Sepas SEC 250 column. The column was washed to the base line with an equilibrium buffer solution (25 mM HEPES, 500 mM NaCl, 2% glycerol, 0.05 DDM, 0.01% CHS, pH 7.5) before loaded, until no considerable variance. The sample was then added into the special 96-well plate and treated with integration using by the software of the instrument.

Figure 3A:
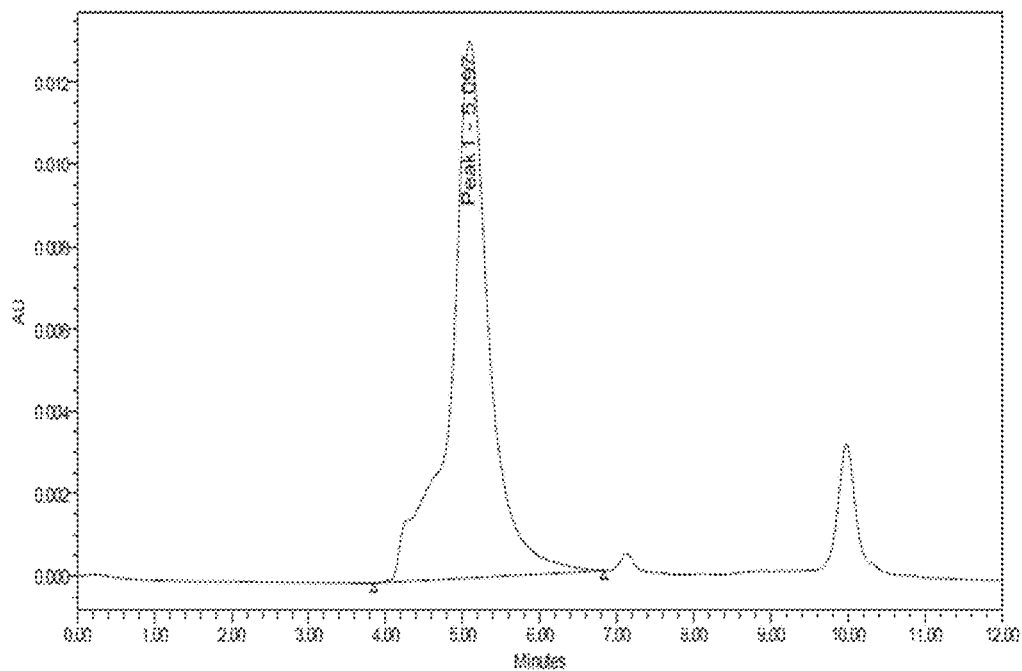
FIG. 3a, Ultra performance liquid chromatography (UPLC) analysis of A2a-APC fusion protein.
Figure 3B:
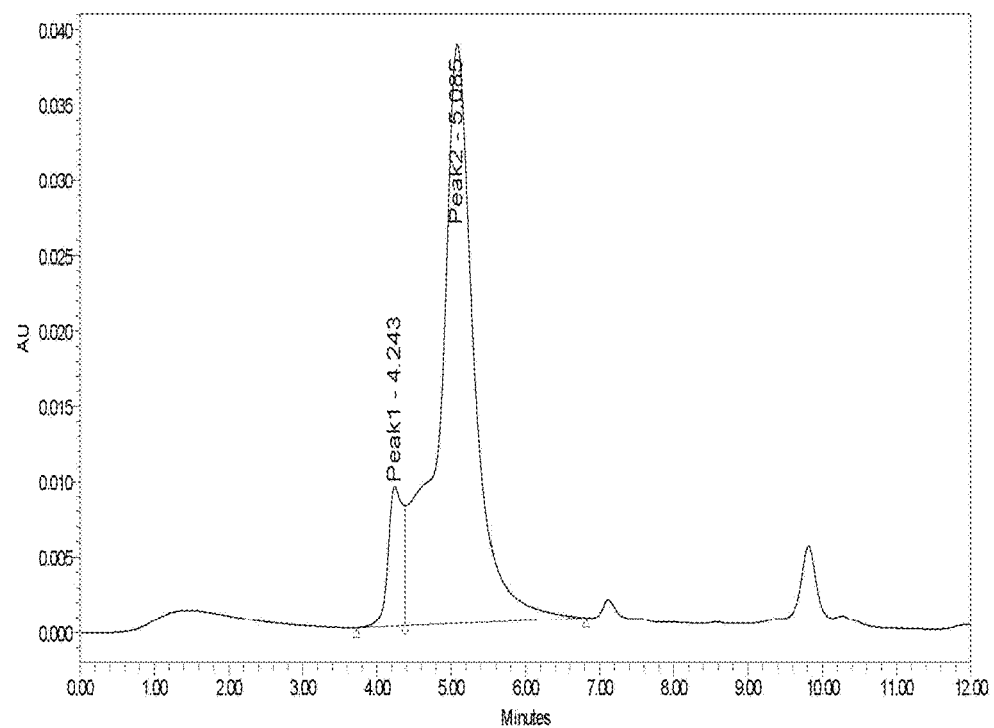
FIG. 3b, UPLC analysis of A2a-RGS16 fusion protein.
Figure 3C:
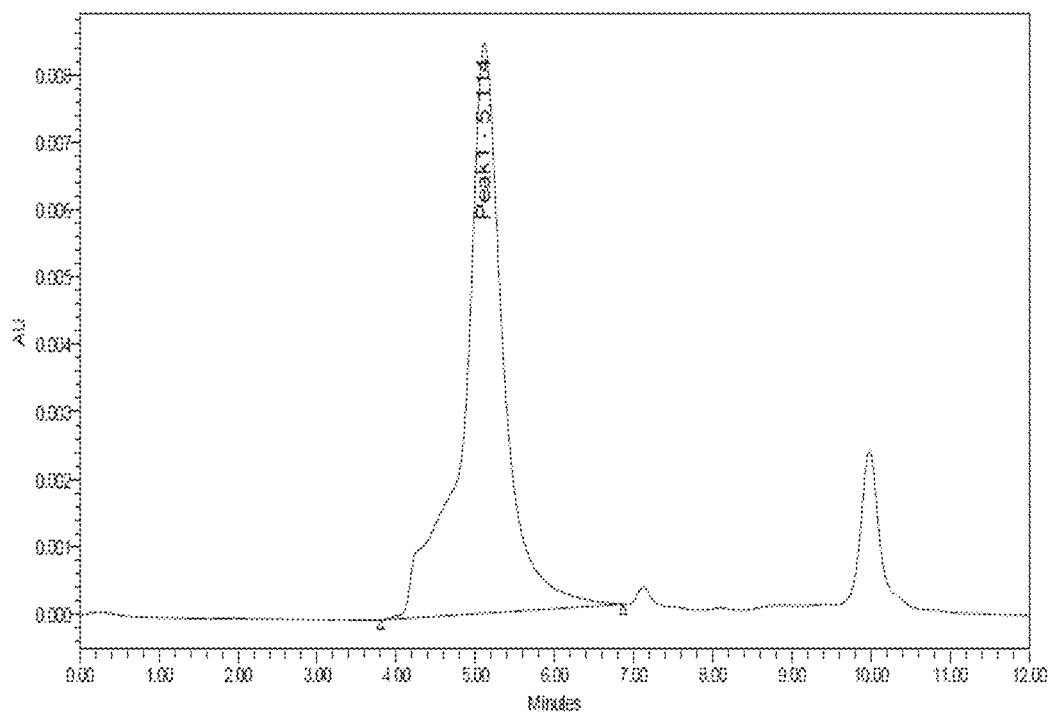
FIG. 3c, UPLC analysis of A2a-DNJ fusion protein.

The three fusion protein samples were detected according to the above method, the results of which are shown in FIG. 3. The three fusion proteins have good homogeneity with single peak which is the major part for the protein samples.

What is claimed is:

1. A nucleic acid molecule encoding a fusion protein comprising a fragment of a G-Protein Coupled Receptor (GPCR) protein and an inserted fragment;
   wherein the GPCR protein is an A2a protein having an amino acid sequence according to SEQ ID NO: 26,
   wherein the inserted fragment comprises an APC protein fragment having an amino acid sequence of SEQ ID NO: 1, a RGS16 protein fragment having an amino acid sequence of SEQ ID NO: 2, or a DNJ protein fragment having an amino acid sequence of SEQ ID NO: 3.

2. The nucleic acid molecule according to claim 1 comprising a nucleotide sequence according to SEQ ID NO: 10, SEQ ID NO: 11, or SEQ ID NO: 12.

3. The nucleic acid molecule according to claim 1 comprising a nucleotide sequence according to SEQ ID NO: 10.

4. The nucleic acid molecule according to claim 1 comprising a nucleotide sequence according to SEQ ID NO: 11.

5. The nucleic acid molecule according to claim 1 comprising a nucleotide sequence according to SEQ ID NO: 12.

* * * * *